United States Patent

Heyrend et al.

[11] Patent Number: 6,115,631
[45] Date of Patent: Sep. 5, 2000

[54] APPARATUS AND METHOD FOR PREDICTING PROBABILITY OF RUMINATING BEHAVIOR IN PEOPLE

[76] Inventors: F. LaMarr Heyrend, 411 N. Allumbaugh; Donald R. Bars, 5121 N. Mountain View, both of Boise, Id. 83704

[21] Appl. No.: 09/215,401

[22] Filed: Dec. 18, 1998

[51] Int. Cl.⁷ .................................................. A61B 5/04
[52] U.S. Cl. .................................................. 600/544
[58] Field of Search ................................ 600/300, 544, 600/595

[56] References Cited

U.S. PATENT DOCUMENTS

| | | | |
|---|---|---|---|
| 4,817,627 | 4/1989 | Cohen et al. | 600/544 |
| 4,955,388 | 9/1990 | Silberstein | 600/544 |
| 5,331,969 | 7/1994 | Silberstein | 600/544 |
| 5,447,166 | 9/1995 | Gevins | 600/544 |
| 5,730,146 | 3/1998 | Itil et al. | 600/544 |
| 5,891,050 | 4/1999 | Gansler | 600/544 |
| 5,983,129 | 11/1999 | Cowan et al. | 600/544 |

*Primary Examiner*—Robert L. Nasser
*Attorney, Agent, or Firm*—Frank Dykas

[57] ABSTRACT

A method and apparatus for determining the probability of ruminating behavior in a person of known age, sex and use of medication, is provided by generating and measuring a visually evoked response to a certain auditory and visually displayed paradigms and measuring the amplitude, in microvolts, of the evoked response for a period of time of approximately 500 milliseconds after cessation of the paradigm displays, and quantifying the absolute values of the delta, theta, alpha and beta frequency bands of a standard EEG, and applying this data to an algorithm to compute on the probability of ruminating behavior.

8 Claims, 3 Drawing Sheets

APPARATUS AND METHOD FOR PREDICTING PROBABILITY OF RUMINATING BEHAVIOR IN PEOPLE

BACKGROUND OF THE INVENTION

1. Technical Field

This invention generally relates to an apparatus and method for predicting the propensity of any individual for exhibiting ruminating behavior by obtaining and processing electroencephalographic information and applying that data to an algorithm to compute the probability of ruminating behavior.

2. Background

Perhaps the best and closest description of rumination behavior is found in the American Psychiatric Association Diagnostic and Statistical Manual of Mental Disorders is listed under Manic Episodes and states: "The individuals thoughts may race, often at a rate faster than can be articulated . . . some individuals with manic episodes report that this experience resembles watching two or three television programs simultaneously. Frequently, there is a flight of ideas evidenced by a nearly continuous flow of accelerated speech, with abrupt changes from one topic to another. When flight of ideas is severe, speech may become disorganized and incoherent." Ruminating behavior is found in those suffering from obsessive compulsive disorders, bi-polar disorders, manic and hypo-manic disorders, depression and attention deficit/hyperactivity disorder.

Rumination in conjunction with obsessive/compulsive and manic disorders are often misdiagnosed as strictly attention-deficit hyperactivity disorder. When misdiagnosed as attention-deficit/hyperactivity disorder, individuals may be erroneously prescribed stimulant medications. Stimulant medications for those suffering from obsessive/compulsive, bipolar and manic disorders is not appropriate, and results in the individual becoming extremely tired and will increase the aggressive, agitated rebound effect in the evenings when the stimulants wear off. When a hypo-manic suffering from rumination is misdiagnosed as attention-deficit/hyperactivity disorder and given stimulant medication, the patient is put at risk psychiatrically and educationally. In effect, it is the misdiagnosis and incorrectly prescribed stimulant which may exacerbate psychotic symptoms or actually induce psychosis. Of the academic environments, such as children at school, such individuals may be more behaviorally compliant, and still suffer decreased cognitive retention, leading to diminished learning potential. In such cases, parents and teachers will typically know that the stimulation medication is not perfect, but is still better than nothing. However, when properly diagnosed, individuals, particularly children suffering from obsessive-compulsive, bi-polar or manic disorders exhibiting ruminating behavior, can be treated effectively.

Accordingly, it is an object of the present invention to provide an apparatus and method for determining the probability that a person is experiencing ruminating behavior as opposed to pure attention-deficit/hyperactivity disorder, and thus to more accurately segregate and appropriately treat these individuals.

It is a further object of this invention to predict the probability of ruminating behavior so as to prevent the misdiagnosis of pure attention deficit/hyperactivity disorder and the resulting inappropriate treatment of the individual with stimulants.

DISCLOSURE OF INVENTION

These objects are achieved using a testing apparatus which includes an EEG Data Acquisition and Analysis System, which is electrically interconnected to a head assembly containing a plurality of EEG electrodes. The output from the EEG Data Acquisition and Analysis System is sent to a microprocessor where two primary functions of the testing system are performed. These are, the quantification of a standard EEG into absolute powers in the delta, theta, alpha and beta frequency bands and the timing, synchronization and averaging of a series of displays of a paradigm generating a visually evoked response.

Also electrically interconnected to the microprocessor is a visual display device for periodically displaying a plurality of sequential, visual paradigms to a test subject. Hard copy output devices, such as a printer and a video output are also interconnected to the microprocessor.

In use, the testing system is used to test for the probability of ruminating behavior. The individual to be tested is first seated comfortably in a chair and sixteen (16) electrodes are attached to the scalp of the individual to be tested in accordance with the International 10-20 System of the American Electroencephalographic Society's guidelines, namely to locations F7, F3, F4, F8, T3, C3, CZ, C4, T4, T5, PE, PZ, P4, T6, 01 and 02. Electrode impedance is maintained at less than 2.0 Kohms and the impedance between homologous sites maintained within 1.0 Kohms. The gain for the EEG Data Acquisition and Analysis System is set at 30,000, with a low pass filter at 100 Hz, and a high pass filter at 1.0 Hz, and a 60 Hz notch filter is set in.

A standard quantitative electroencephalogram is then performed, at which time the EEG Data Acquisition and Analysis System, working in conjunction with the microprocessor, provides a measurement as to the absolute power of the electroencephalograph in the delta, theta, alpha and beta frequency bands, all in the absence of any visual or auditory stimulus.

Next, a visually evoked potential test is conducted using a visual evoked flash paradigm displayed on the visual device at eye level, 76 cm in front of the individual being tested. The pattern is reversed every 0.59 seconds for a total of 1.7 stimuli per second. A 512 millisecond epoch is utilized with a five millisecond pre-stimulus time. The intensity of the background stimulus is 12.69 candelas per square meter, and the flash is 19.26 candelas per square meter. The test subject is instructed to visually fixate on a red dot centered on the visual device, is requested not to speak, and to remain relaxed with as little movement as possible throughout the two minutes of recording time.

The visually evoked response to each display of a paradigm, as recorded by the EEG Data Acquisition and Analysis System, is then recorded in the microprocessor in a synchronized manner with the time of the display of the paradigm and then averaged together to cancel out the potentials of brain activities that are not related to the visually evoked response, thus generating, in microvolts, the potential of the visually evoked response over a period of time from immediately prior to the display of the paradigm to the time of approximately 500 milliseconds after cessation of the displayed paradigm.

An auditory evoked potential is also generated by utilizing an oddball paradigm as stimuli consisting of rarefacted tones. Three trials are completed using 1.7 and 1.1 stimuli per second with a 512 ms epoch and a 0.9 stimuli per second with a 1024 milliseconds epoch. Standard tones of 1000 Hz and infrequent tones of 2000 Hz are presented bi-naturally at 75 decibels on headphones. The rise and fall time is 10 milliseconds with a 40 millisecond plateau. The target tone is the 2000 Hz tone, and it occurs twenty-five percent of the time, randomly, and is counted by the subject using a hand-held mechanical counter. A practice trial is first completed allowing the individual to become accustomed to the differences between tones. The individual's tally on the mechanical counter is compared with the computer generated count for accuracy and the difference recorded. During all trials, the individual is encouraged to count the exact number of target tones presented. The individuals are requested to keep their eyes closed, with minimum movement, and to remain as relaxed as possible. Artifacts are detected and removed using an on-line artifact rejection program. Fifty artifact-free trials of the target tone and a minimum of 200 standard tones are used to produce the final wave forms.

The test subject is also interviewed, or in some other way, certain biographical and medical data is acquired for use in the analysis conducted in the microprocessor to determine the probability of ruminating behavior. The information required is the identification on the sex of the test subject, the test subject's age, and a medical history of the test subject, including whether or not the test subject is currently taking any medications, and whether the test subject is experiencing racing thoughts, impulsive behavior problems, falling asleep or remaining asleep, scattered thoughts, and distractibility caused by an inability to stay focused.

Next, one of three algorithms are applied to the data. The first algorithm is applicable to any test subject, irrespective of whether or not the test subject is using medication or other drugs at the time of testing. This algorithm is: $\ln(P[\text{ruminating}])=-0.3489+(-0.00608*\text{age})+(-0.6282*\text{sex})+0.3597*\text{meds}+1.9192*\ln\text{DeltaF4}+(-1.0375*\ln\text{DeltaO1})+(-1.0488*\ln\text{DeltaCZ})+(-0.1899*\text{maxP50})+0.15*\text{maxP200}$. In it: age means the test subject's age in years; sex means, in the case of a male test subject, the value of 0, and in the case of a female test subject the value of 1; meds means, in case the individual is taking medication, a value of 1, and in the case where the test subject is not taking medication, a value of 0; and lnDeltaF4 means the natural log of the absolute value, in microvolts of the Delta wave band, as taken at the electrode placement location F4 as shown in FIG. 2; lnDeltaO1 means the natural log of the absolute value, in microvolts of the Delta wave band, as taken at the electrode placement location O1 as shown in FIG. 2; lnDeltaCZ means the natural log of the absolute value, in microvolts of the Delta wave band, as taken at the electrode placement location CZ as shown in FIG. 2; MaxP50 means the maximum positive voltage potential at either the F3 or F4 electrodes, in microvolts, of the auditory evoked response at a time of approximately 50 milliseconds after termination of the standard tone of the P300 oddball paradigms as averaged as previously described; and MaxP200 means the maximum positive voltage potential at either the F3 or F4 electrodes, in microvolts, of the visually evoked response at a time of approximately 200 milliseconds after termination of the visual display of the paradigms as averaged as previously described. It can be used to determine a probability of ruminating behavior irrespective of the age, sex or medical condition of the test subject by taking $e^{\ln(P[\text{ruminating}])}$.

In the case where it is reliably determined that the test subject is not on medication, then a second algorithm can be applied to the data. The second algorithm is: $\ln(P[\text{ruminating}])=-8.0738+0.4767*\text{age}+0.7528*\text{sex}+2.2807*\ln\text{DeltaF4}+(-2.1726*\ln\text{DeltaCZ})+0.6963*\text{maxP200}+(-0.0401*\text{age}*\text{maxP200})$. The terms previously defined for the first algorithm remain the same.

In the event that it can be reliably determined that the test subject is on medication at the time of testing, then a third algorithm may be used, as follows: $\ln(P[\text{ruminating}])=+1.7726+(-0.1044*\text{age})+0.6774*\text{sex}+2.0495*\ln\text{DeltaF3})+(-1.993*\ln\text{DeltaO1})+(-0.1199*\text{maxP100})+0.157*\text{maxP200}$, with the definitions again being the same as for the first and second algorithms taken at various different electrode placements and maxP100means the maximum positive voltage potential at either electrode O1 or O2, in microvolts, of the visually evoked response at a time of approximately 100 milliseconds after termination of the visual display of the paradigms as averaged as previously described.

In each case, the probability of ruminating behavior can then be determined by taking $e^{\ln(P[\text{ruminating}])}$.

BEST MODE FOR CARRYING OUT INVENTION

What follows is a description of an apparatus and method of testing individuals to determine a probability of future ruminating behavior. While this apparatus is used to determine a probability of future ruminating behavior with a high degree of concordance between test results and clinical evaluations, the absence of positive test results, that is to say a finding of low probability of ruminating behavior, does not mean that the tested individual is not predisposed toward ruminating behavior, as there are many factors, biological and environmental, which can create multiple paths and mechanisms which can result in an individual's manifestation of ruminating behavior.

Figure 1:
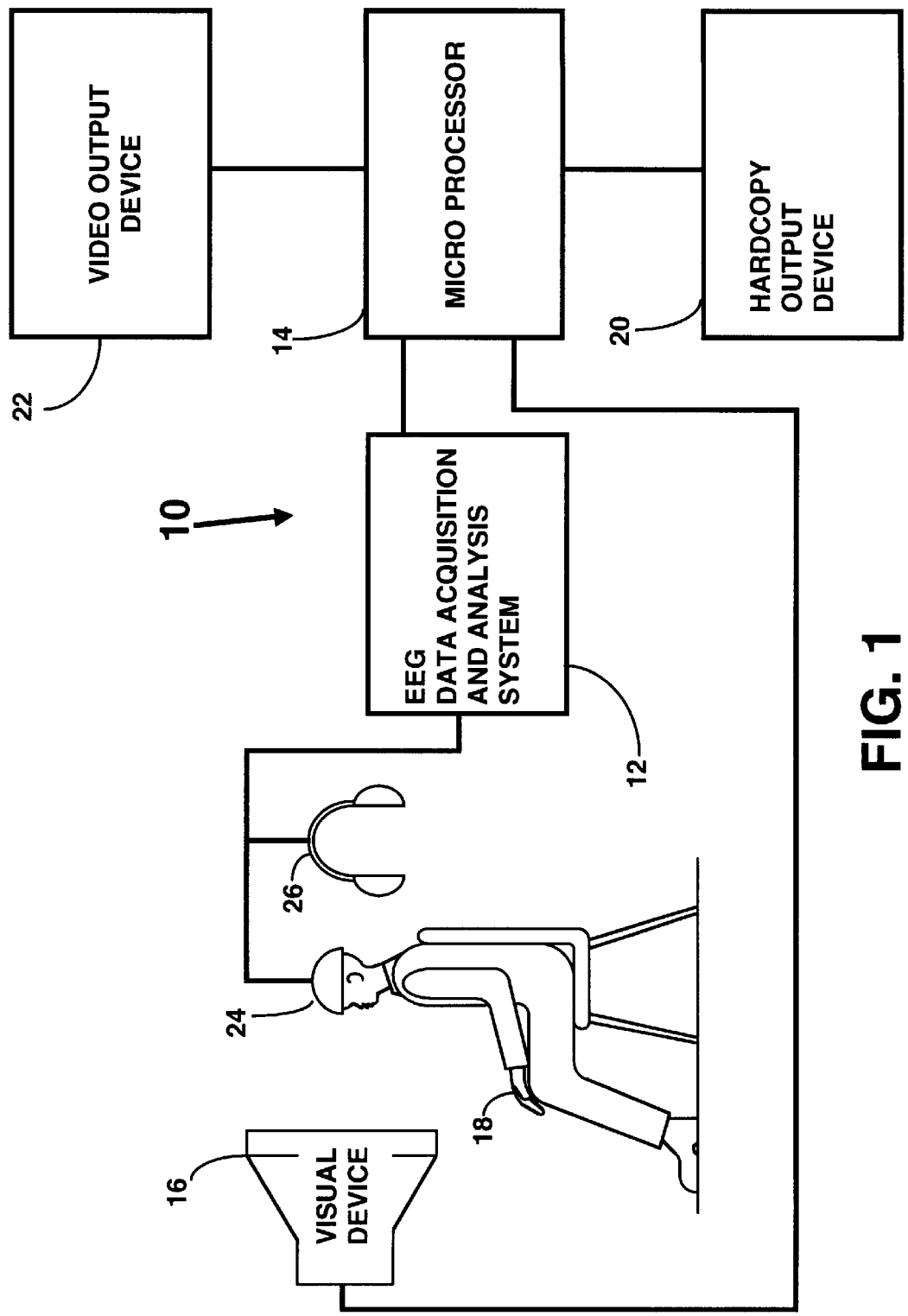
FIG. 1 is a representational schematic of the testing apparatus.

Referring now to FIG. 1, there is shown in representational schematic format the apparatus, or testing system 10. At the heart of testing system 10 is EEG Data Acquisition and Analysis System 12, which is electrically interconnected to a head assembly 24 containing a plurality of EEG electrodes. EEG Data Acquisition and Analysis System 12 output is sent to microprocessor 14 where two primary functions of the testing system 10 are performed.

Also electrically interconnected to microprocessor 14 are visual device 16 and headphones 26. Visual device 16 is used to periodically display a plurality of sequential visual paradigms to test subject 18. The two functions performed in microprocessor 14 are the quantification of a standard EEG into absolute powers in delta, theta, alpha and beta frequency bands, and the second function being the timing, synchronization and averaging of visually evoked responses to a periodic display of a paradigm using visual device 16. Averaging is used to average out random waves and thus quantify the actual visual evoked response over a period of time relative to each of the sequential paradigm displays.

In a like manner, headphones 26 are used in conjunction with microprocessor 14 in order to produce a synchronized and averaged auditory evoked response, responsive to a P300-oddball paradigm, as is later described.

Hard copy output device 20 is also provided, and typically is a standard printer capable of generating tables of data and accurate graphic displays. Video output device 22, typically a standard high resolution video display screen is used for real time displays of the same data.

Figure 2:
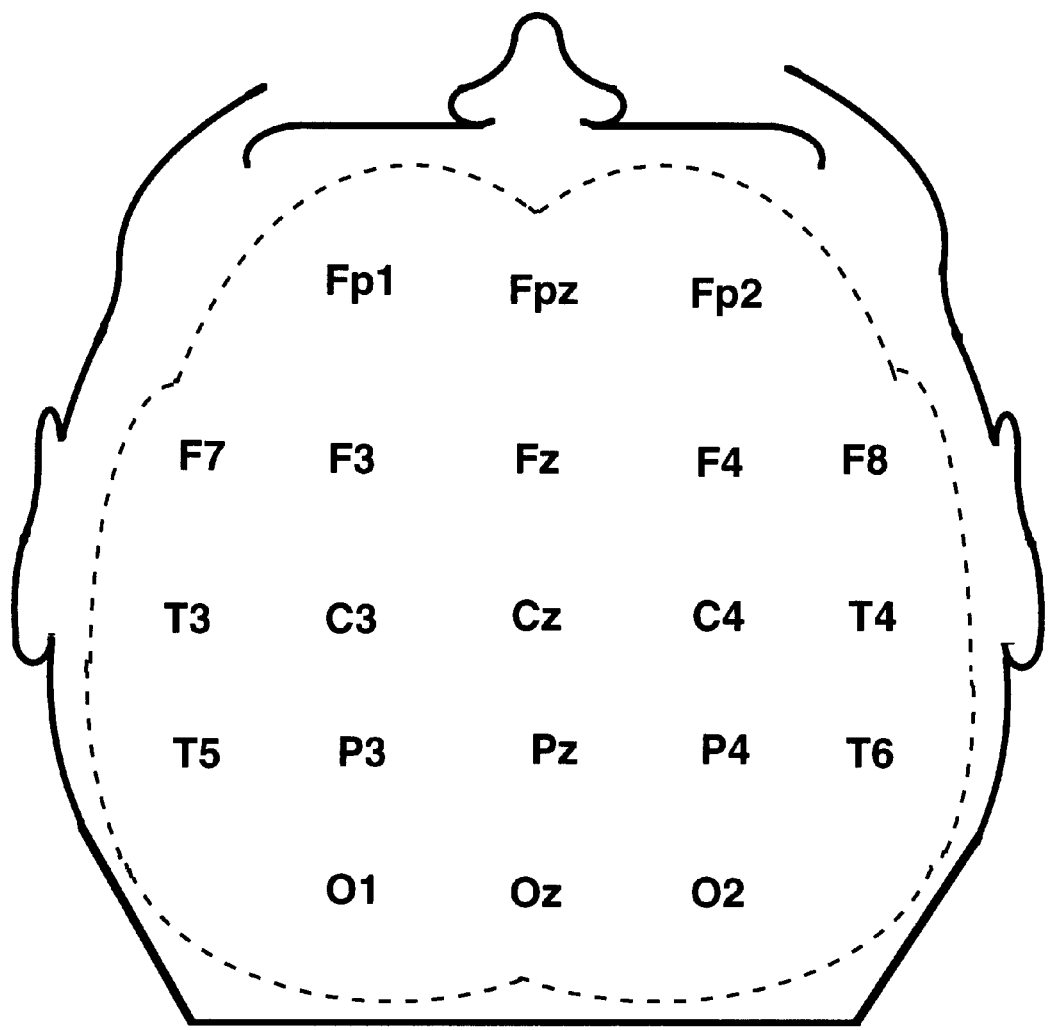
FIG. 2 is a representational map of the scalp of a person showing the location and designator for standard electrodes at standard sites in accordance with the American Electroencephalographic Society's Electrode Placement International 10-20 Standard System for measuring a person's brain waves.

To use system 10 to test for the probability of ruminating behavior, the individual to be tested, 18, is first seated comfortably in a chair and sixteen electrodes contained within head assembly 24 are attached to the scalp of the individual to be tested in accordance with the International 10-20 System of the American Electroencephalographic Society's guidelines, namely to locations F7, F3, F4, F8, T3, C3, CZ, C4, T4, T5, P3, PZ, P4, T6, 01 and 02, as shown in FIG. 2. Electrode impedance is maintained at less than 2.0 Kohms and the impedance between homologous sites maintained within 1.0 Kohms. The gain for EEG Data Acquisition and Analysis System 12 is set at 30,000, with a low pass filter at 100 Hz, and the high pass filter at 1.0 Hz, and a 60 Hz notch filter is set in.

A standard quantitative electroencephalogram is then performed, at which time EEG Data Acquisition and Analysis System 12, working in conjunction with microprocessor 14, provides a measurement as to the absolute power of the electroencephalo-graph, in delta, theta, alpha and beta frequency bands, all in the absence of any visual or auditory stimulus. This may all be accomplished in accordance with the teachings of U.S. Pat. No. 4,862,359, dated Aug. 29, 1989, the teachings of which are herein incorporated by reference.

Next, a visually evoked potential test is conducted using a flash visual evoked paradigm displayed on visual device 16 at eye level, and 76 cm in front of test subject individual 18. The paradigm is flashed every 0.59 seconds for a total of 1.7 stimuli per second. A 512 millisecond (ms) epoch is utilized with a five ms pre-stimulus time. The intensity of the background stimulus is 12.69 candelas per square meter ($cd/m^2$), and the flash is 19.26 $cd/m^2$. The test subject 18 is instructed to visually fixate on a red dot centered on visual device 16, is requested not to speak, and to remain relaxed with as little movement as possible throughout the two minutes of recording time.

The visually evoked response to each display of a paradigm, as recorded by EEG Data Acquisition and Analysis System 12, is then recorded in microprocessor 14 in a synchronized manner with the time of the display of the paradigm, and then averaged together, to cancel out the potentials of brain activities that are not related to the visually evoked response, thus generating, in microvolts, the potential of the visually evoked response over a period of time from immediately prior to the display of the paradigm to the time of approximately 500 milliseconds after cessation of the displayed paradigm.

An auditory evoked potential is generated using an oddball paradigm having stimuli consisting of rarefacted tones. Three trials are completed using 1.1 and 1.7 stimuli per second, with a 512 millisecond epoch and a 0.9 stimuli per second having a 1024 millisecond epoch. Standard tones are 1000 Hz, and infrequent tones, which are the target tones, are 2000 Hz. These are presented bi-naturally at 75 decibels on headphones 26. The rise and fall time is 10 milliseconds with a 40 millisecond tone. The target tone occurs twenty-five percent of the time in a random manner, and is counted by the subject using a hand-held mechanical counter. A practice trial is completed, allowing the individual to become accustomed to the difference between tones. The individual's tally is compared with the computer generated count for accuracy and the difference recorded. During all trials, the individual 18 is encouraged to count the exact number of target tones presented. Individuals 18 are then requested to keep their eyes closed, with minimum movement, and to remain as relaxed as possible. Artifacts are detected and removed, using an on-line artifact rejection program. Fifty artifact free trials of the target tone, and a minimum of 200 standard tones are used to produce the final wave forms.

The test subject 18 is also interviewed, or in some other way, certain biographical and medical data is acquired for use in the analysis conducted in microprocessor 14 to determine the probability of ruminating behavior. The information required is the identification on the sex of the test subject, the test subject's age, in years, and a medical history as to whether or not the test subject is currently taking medications such as anti-depressants, anti-convulsants, alpha blockers, stimulants, lithium, tricyclic anti-depressants, or any other type of drug or medication.

Next, in the preferred embodiment of the present invention, one of three algorithms is applied in microprocessor 14 to the data collected to determine a probability for ruminating behavior. These Algorithms are as follows:

A first algorithm may be used irrespective of whether test subject 18 is, or is not, using medication or other drugs at the time of testing. The first algorithm is: $\ln(P[\text{ruminating}]) = -0.3489 + (-0.00608 * \text{age}) + (-0.6282 * \text{sex}) + 0.3597 * \text{meds} + 1.9192 * \ln\text{DeltaF4} + (-1.0375 * \ln\text{DeltaO1}) + (-1.0488 * \ln\text{DeltaCZ}) + (-0.1899 * \text{maxP50}) + 0.15 * \text{maxP200}$. In it: age means the test subject's age in years; sex means, in the case of a male test subject, the value of 0, and in the case of a female test subject the value of 1; meds means, in case the individual is taking medication, a value of 1, and in the case where the test subject is not taking medication, a value of 0; and lnDeltaF4 means the natural log of the absolute value, in microvolts of the Delta wave band, as taken at the electrode placement location F4 as shown in FIG. 2; lnDeltaO1 means the natural log of the absolute value, in microvolts of the Delta wave band, as taken at the electrode placement location O1 as shown in FIG. 2; lnDeltaCZ means the natural log of the absolute value, in microvolts of the Delta wave band, as taken at the electrode placement location CZ as shown in FIG. 2; MaxP50 means the maximum positive voltage potential at either the F3 or F4 electrodes, in microvolts, of the auditory evoked response at a time of approximately 50 milliseconds after termination of the standard tone of the P300 oddball paradigms as averaged as previously described; and MaxP200 means the maximum positive voltage potential at either the F3 or F4 electrodes, in microvolts, of the visually evoked response at a time of approximately 200 milliseconds after termination of the visual display of the paradigms as averaged as previously described.

In the case where it is reliably determined that the test subject is not on medication at the time of testing, then, in the preferred embodiment, the following algorithm may be applied to the data obtained from testing system 10 to determine the probability of ruminating behavior, as follows: $\ln(P[\text{ruminating}]) = -8.0738 + 0.4767 * \text{age} + 0.7528 * \text{sex} + 2.2807 * \ln\text{DeltaF4} + (-2.1726 * \ln\text{DeltaCZ}) + 0.6963 * \text{maxP200} + (-0.0401 * \text{age} * \text{maxP200})$. The terms previously defined for the first algorithm remain the same.

In the event it can be reliably determined that the test subject is on medication at the time of testing, then a third algorithm may be used, as follows: $\ln(P[\text{ruminating}]) = +1.7726 + (-0.1044 * \text{age}) + 0.6774 * \text{sex} + 2.0495 * \ln\text{DeltaF3}) + (-$ 1.993*lnDeltaO1)+(−0.1199*maxP100)+0.157*maxP200, with the definitions again being the same as for the first and second algorithms taken at various different electrode placements and maxP100 means the maximum positive voltage potential at either the O1 or O2 electrodes, in microvolts, of the visually evoked response at a time of approximately 100 milliseconds after termination of the visual display of the paradigms as averaged as previously described.

In practice it has been found that the determination of the maximum potential of the visually evoked response, in microvolts, at approximately 200 milliseconds after termination of the stimulus of the visual display of the paradigm at the F3 and F4 electrodes is a most significant indicator of the probability of ruminating behavior for those tested individuals who are determined not to be taking medication at the time of testing and for those who are taking medication at the time of testing, and, if the first algorithm is used, for any individual irrespective of whether medication is being used or not. In fact, it appears, as the amplitude of the visually evoked response at approximately 200 milliseconds after termination of the stimulus increases, the percentage of probability of ruminating behavior correspondingly increases, and at amplitudes greater than 18 microvolts, there appears to be a 100% probability of future ruminating behavior in the tested individual.

These results and the algorithms used were tested on a test group of children and adolescents selected from a group of 454 children. Complete medical data and clinical evaluations were available for 326 of the children, which became the test group. One hundred ninety seven were not on medication at the time they were subjected to testing through system 10. In the study were 105 females and 221 males, of which 60 females and 137 males with an average age of 13.49 years were ruminating, with the remainder not testing positive for ruminating behavior and of an average of 12.76 years.

Each patient was administered a series of evoked potential studies and a quantitative electroencephalogram, in accordance with the American Electroencephalographic Society's Guidelines, utilizing the Brain Atlas III® of the Bio-Logic Systems Corporation, Chicago, Ill. Electrode placements were in accordance with the International 10-20 system, using an Electro-Cap®, with 16 active electrodes; F7, F3, F4, F8, T3, C3, CZ, C4, T4, T5, P3, PZ, P4, T6, O1, and O2. A monopolar montage with forehead ground was utilized with linked ear reference. Electrode impedance was maintained less than 2.0 Kohms and the impedance between homologous sites maintained within 1.0 Kohms. The gain was set at 30,000, the low pass filter at 100 Hz, the high pass filter at 1.0 Hz, and the 60 Hz notch filter was set in. Patients were comfortably seated in a padded reclining chair in a small, sound attenuated room. A channel-by-channel calibration was performed before and after each recording session.

The electrophysiological test series consisted of: (1) four visual evoked potentials (VEP), pattern reversal (both eyes, left eye, right eye), and flash (both eyes); (2) three auditory evoked potentials (AEP) which is commonly known as the odd ball paradigm at 3 different speeds; (3) two brainstem auditory evoked potentials (BAER); and (4) twenty minutes (post 2 minutes hyperventilation) of computerized electroencephalogram (CEEG). The digital EEG data was evaluated and artifact free data was used to create eyes open and eyes closed (resting) Fast Fourier Transformed files (FFT). All of the VEP's, some AEP and the FFT files were analyzed in the study.

The pattern/reversal visual evoked potential was recorded from each individual in accordance with the American Electroencephalographic Society's Guidelines. The checkerboard pattern/reversal paradigm utilized 19 millimeter, black and white alternating squares displayed on a model TC1115 RCA monitor positioned at eye level, 76 centimeters in front of the patient and subtending at a visual angle of 23 degrees. The pattern reversed every 0.59 seconds for a total of 1.7 stimuli per second. A 256 millisecond (ms) epoch was utilized with a five ms pre-stimulus time. The flash paradigm utilized a 512 ms epoch with 10 ms of pre-stimulus time. The intensity of stimulus from the checkerboard pattern/reversal was 12.69 candelas per square meter ($cd/m^2$) and the flash 19.26 $cd/m^2$. The patient was instructed to visually fixate on a red dot, centered on the RCA monitor, requested not to speak, and, to remain relaxed with as little movement as possible throughout the two minutes of recording time. Artifacts were detected and removed using the Bio-Logic on-line artifact reject program. For each patient, two hundred artifact-free trials were averaged together to produce the final waveform.

All patient clinical files were reviewed for presence of: head injuries, loss of consciousness, or ruminating behaviors, defined as any mention of: racing thoughts, impulsive behaviors, problems of either falling asleep or remaining asleep, scattered thoughts and distractibility caused by inability to stay focused. These variables were evaluated across the flash averaged visually evoked potential amplitude measured in positive amplitude, measured in microvolts, at approximately 200 ms after termination of the stimulus (P200), recorded over the frontal lobes by F3 and F4 scalp electrodes, the common method of recording this phenomenon.

Logistic regression analysis was then used to determine if the response variable, explosivity, was significantly associated with any of 34 predictor variables measured, namely a history of head injury, loss of consciousness, sex, age, maximum amplitude of the P200 wave form and the absolute power of the delta, theta, alpha and beta frequency bandwidth. Ruminating behaviors were found in 154 (48%) of the 326 patients in the study, 88, or 45% of the 197 patients not on medication at the time of their study.

Figure 3:
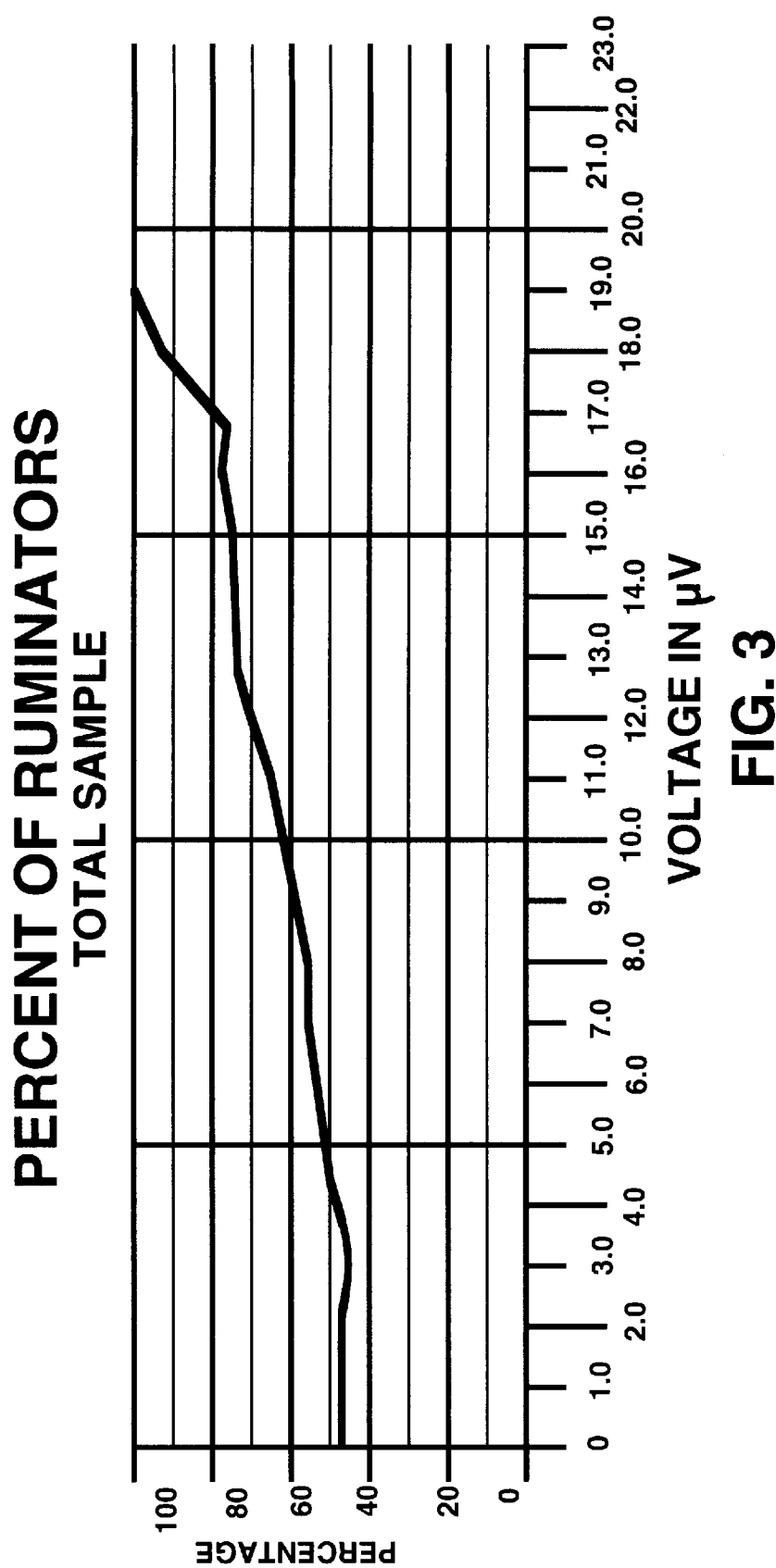
FIG. 3 is a graph showing the percentage of ruminating individuals in relationship to the amplitude of the visually evoked potentials at 200 milliseconds after termination of the display of the paradigm.

The highest voltage recorded during the VEP, at either F3 or F4 electrodes was analyzed for each patient. Patients qualifying as ruminating were significantly more likely to have increased P200 amplitude values ($\chi^2=19.7635$, df=1; p<0.0001) and there were significantly more males ($\chi^2=5.4558$, df=1; p<0.0195). The ruminating patients averaged 9.06 mV (SD=5.2) and the non-ruminating patients averaged 7.08 mV (SD=3.46). Evaluating the data on the nonmedicated patients again showed a relationship between an increase in amplitude of the P200 and ruminating behavior ($\chi^2=9.2144$, df=1; p<0.0024). The variable of sex was only slightly significant ($\chi^2=4.6401$, df=1); p<0.0312). The ruminating patients averaged 9.59 $\mu V$ (SD=5.1) and the non-ruminating patients averaged 7.17 $\mu V$ (SD=3.45). FIG. 3 depicts the percentage of ruminating patients based upon the amplitude of the P200 wave form. It shows that 50% of the ruminating patients in our study produce a P200 wave form of 6.0 $\mu V$ or greater.

Our testing showed that high amplitude P200 wave forms are significantly associated with the behavior exhibited by one subset of ruminating individuals. We believe that this wave form, which occurs within the obligatory portion of the brain's electrophysiological response to sensory stimulation, approximately within the first 200 milliseconds, post stimulus, is a biological signature and represents an individual's unique biological predisposition to respond to some environmental stimuli in a given manner, namely with ruminating thoughts. We have also shown that this relationship and its significance does not change when patients on medication are included in the statistical analysis. The study strongly suggests that many individuals exhibiting ruminating behaviors have an organic predisposition for ruminating behavior which is an innate characteristic of their central nervous system and that the use of non-invasive visual evoked potentials can accurately identify this group of biologically based ruminating disorders.

Concordance testing was then conducted, in which all possible paring of individuals with ruminating behavior present and ruminating behavior absent were created. A pair was defined as concordant if the individual with ruminating behavior present was also the individual predicted by the logistical regression models of the aforementioned algorithms to be an individual more likely to have ruminating behavior present, based upon physiological predicted variables, primarily the amplitude of the visually evoked potential at approximately 200 milliseconds after stimulus. A pair was discordant if the model incorrectly predicted that the individual with ruminating behavior absent was more likely to be the individual with ruminating behavior present. The percentages of the total number of pairs that were concordant was 73.5%, and discordant 26.2%.

It should be apparent to those skilled in the art that if a different paradigm or paradigm display procedure were to be used, a different visually evoked response would be generated. However, while this may generate a different set of significant variables in the algorithms, standard logistical regression analysis procedures could be used, as set forth above, to generate similar algorithms to those set forth in this preferred embodiment, which in and of themselves may be of similar high reliability.

While there is shown and described the present preferred embodiment of the invention, it is to be distinctly understood that this invention is not limited thereto but may be variously embodied to practice within the scope of the following claims.

We claim:

1. A method of determining the probability of ruminating behavior in a person of known age, sex and use of medication, using an electroencephalographic machine operable for reading human brain waves, a computer operable for receiving the output of said electroencephalographic machine, a device operable to display a paradigm of a pre-selected design, illumination, and frequency, said computer also capable of synchronizing the recording and averaging said brain waves when the paradigm is illuminated, which comprises:

attaching the electrodes of an electroencephalographic machine to the scalp of said person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of the displayed paradigms during the time of display;

averaging said brain waves to determine the visually evoked response to said displays of said paradigms;

measuring the maximum amplitude, in microvolts, of said visually evoked response at a plurality of points in time over approximately 500 ms of time after termination of each of the displays of said paradigms;

transmitting to said person a plurality of audio signals and simultaneously measuring the brain waves of said person for each of the audio signals during the time said auditory signals are being transmitted;

averaging said brain waves to determine the auditory evoked response to said transmissions of said audio signals;

measuring the maximum amplitude, in microvolts, of said auditory evoked response at a plurality of points in time over approximately 500 ms of time after termination of each of the transmissions of said audio signals;

conducting and recording the quantitative electroencephalographic activity of said person;

measuring the amplitude of said quantitative electroencephalographic activity;

conducting a logistic regression analysis of said visually evoked response over a period of time of approximately 500 ms after termination of each of said displays of said paradigm, said auditory evoked response over a period of time of approximately 500 ms after termination of said transmission of said audio signals, said electroencephalographic activity, and said person's age, sex, and whether said person is taking medication, to establish a predictive algorithm; and computing the probability of ruminating behavior using said algorithm.

2. The method of claim 1 wherein the steps of conducting a logistic regression analysis of said visually evoked response over a period of time of approximately 500 ms after termination of each of said displays of said paradigm, said auditory evoked response over a period of time of approximately 500 ms after termination of said transmission of said audio signals, said absolute power of said quantitative electroencephalographic activity, and said person's age, sex, and whether said person is taking any medication, to establish a predictive algorithm, and computing the probability of ruminating behavior using said algorithm further comprise:

measuring the absolute power of the Delta frequency band at electrodes F4, O1 and CZ; and computing the probability of ruminating behavior using the algorithm $\ln(P[\text{ruminating}])=-0.3489+(-0.00608*\text{age})+(-0.6282*\text{sex})+0.3597*\text{meds}+1.9192*\ln\text{DeltaF4}+(-1.0375*\ln\text{DeltaO1})+(-1.0488*\ln\text{DeltaCZ})+(-0.1899*\text{maxP50})+0.15*\text{maxP200}$, wherein age means the test subject's age in years, sex means, in the case of a male test subject, the value of 0, and in the case of a female test subject the value of 1, meds means, in case the individual is taking medication, a value of 1, and in the case where the test subject is not taking medication, a value of 0, lnDeltaF4 means the natural log of the absolute value, in microvolts of the Delta wave band, as taken at the electrode placement location F4, lnDeltaO1 means the natural log of the absolute value, in microvolts of the Delta wave band, as taken at the electrode placement location O1, lnDeltaCZ means the natural log of the absolute value, in microvolts of the Delta wave band, as taken at the electrode placement location CZ, MaxP50 means the maximum positive voltage potential at either the F3 or F4 electrodes, in microvolts, of the auditory evoked response at a time of approximately 50 milliseconds after termination of the standard tone of the P300 oddball paradigms, and MaxP200 means the maximum positive voltage potential at either the F3 or F4 electrodes, in microvolts, of the visually evoked response at a time of approximately 200 milliseconds after termination of the visual display of the paradigms.

3. An apparatus for determining the probability of ruminating behavior in a person of know age, sex and use of medication, which comprises:

an electroencephalographic machine having a plurality of electrodes for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked response to said displays of said paradigms;

means for assessing the maximum amplitude, in microvolts, of said visually evoked response over a period of time of approximately 500 ms after termination of each of said displays of said paradigms;

means for assessing the absolute power of the quantitative electroencephalographic activity;

means for conducting a logistic regression analysis of said visually evoked response and said auditory evoked response over a period of time of approximately 500 ms after termination of each of said displays of said paradigms, said electroencephalographic activity, and said person's age, sex, and whether said person is taking any medication, to establish a predictive algorithm;

means for computing the probability of ruminating behavior using said algorithm.

4. The apparatus of claim 3 wherein said means for conducting a logistic regression analysis of said visually evoked response and auditory evoked response over a period of time of approximately 500 ms after termination of each of said displays of said paradigm, said electroencephalographic activity, and said person's age, sex, and whether said person is taking any medication, to establish a predictive algorithm, and means for computing the probability of ruminating behavior using said algorithm further comprise:

means for measuring the absolute power of the Delta wave at electrodes F4, O1 and CZ; and means for computing the probability of ruminating behavior using the algorithm $\ln(P[\text{ruminating}]) = -0.3489 + (-0.00608 \ast \text{age}) + (-0.6282 \ast \text{sex}) + 0.3597 \ast \text{meds} + 1.9192 \ast \ln\text{DeltaF4} + (-1.0375 \ast \ln\text{DeltaO1}) + (-1.0488 \ast \ln\text{DeltaCZ}) + (-0.1899 \ast \text{maxP50}) + 0.15 \ast \text{maxP200}$, wherein age means the test subject's age in years, sex means, in the case of a male test subject, the value of 0, and in the case of a female test subject the value of 1, meds means, in case the individual is taking medication, a value of 1, and in the case where the test subject is not taking medication, a value of 0, lnDeltaF4 means the natural log of the absolute value, in microvolts of the Delta wave band, as taken at the electrode placement location F4, lnDeltaO1 means the natural log of the absolute value, in microvolts of the Delta wave band, as taken at the electrode placement location O1, lnDeltaCZ means the natural log of the absolute value, in microvolts of the Delta wave band, as taken at the electrode placement location CZ, MaxP50 means the maximum positive voltage potential at either the F3 or F4 electrodes, in microvolts, of the auditory evoked response at a time of approximately 50 milliseconds after termination of the standard tone of the P300 oddball paradigms, and MaxP200 means the maximum positive voltage potential at either the F3 or F4 electrodes, in microvolts, of the visually evoked response at a time of approximately 200 milliseconds after termination of the visual display of the paradigms.

5. A method of determining the probability of ruminating behavior in a person of known age, sex and known not to be using medication at the time of testing, using an electroencephalographic machine operable for reading human brain waves, a computer operable for receiving the output of said electroencephalographic machine, a device operable to display a paradigm of a pre-selected design, illumination, and frequency, said computer also capable of synchronizing the recording and averaging said brains waves when the paradigm is illuminated, which comprises:

attaching the electrodes of an electroencephalographic machine to the scalp of a person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of said displayed paradigms during the time of display;

averaging said brain waves to determine the visually evoked response to said displays of said paradigms;

measuring the maximum amplitude, in microvolts, of said visually evoked response over a period of time of approximately 500 ms after termination of each of said displays of said paradigms;

transmitting to said person a plurality of audio signals and simultaneously measuring the brain waves of said person for each of the audio signals during the time said auditory signals are being transmitted;

averaging said brain waves to determine the auditory evoked response to said transmissions of said audio signals;

measuring the maximum amplitude, in microvolts, of said auditory evoked response at a plurality of points in time over approximately 500 ms of time after termination of each of the transmissions of said audio signals;

measuring the absolute power of the Alpha frequency band at electrode F3 and the Delta frequency band at electrodes F4 CZ; and computing the probability of ruminating behavior using the algorithm $\ln(P[\text{ruminating}]) = -8.0738 + 0.4767 \ast \text{age} + 0.7528 \ast \text{sex} + 2.2807 \ast \ln\text{DeltaF4} + (-2.1726 \ast \ln\text{DeltaCZ}) + 0.6963 \ast \text{maxP200} + (-0.0401 \ast \text{age} \ast \text{maxP200})$, wherein age means the test subject's age in years, sex means, in the case of a male test subject, the value of 0, and in the case of a female test subject the value of 1, lnDeltaF4 means the natural log of the absolute value, in microvolts of the Delta wave band, as taken at the electrode placement location F4, lnDeltaCZ means the natural log of the absolute value, in microvolts of the Delta wave band, as taken at the electrode placement location CZ, and MaxP200 means the maximum positive voltage potential, in microvolts at either the F3 or F4 electrodes, of the visually evoked response at a time of approximately 200 milliseconds after termination of the visual of said paradigms.

6. An apparatus for determining the probability of ruminating behavior in a person of known age, sex and known not to be using medication, which comprises:

an electroencephalographic machine having a plurality of electrodes for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked response to said displays of said paradigms;

means for assessing the maximum amplitude, in microvolts, of said visually evoked response over a period of time of approximately 500 ms after termination of each of said displays of said paradigms;

means for transmitting to said person a plurality of audio signals and simultaneously measuring the brain waves of said person for each of the audio signals during the time said auditory signals are being transmitted;

means for averaging said brain waves to determine the auditory evoked response to said transmissions of said audio signals;

means for measuring the maximum amplitude, in microvolts, of said auditory evoked response at a plurality of points in time over approximately 500 ms of time after termination of each of the transmissions of said audio signals;

means for measuring the amplitude of the Delta wave at electrodes F4 and CZ; and means for computing the probability of ruminating behavior using the algorithm ln(P[ruminating])=−8.0738+0.4767*age+0.7528*sex+2.2807*lnDeltaF4+(−2.1726*lnDeltaCZ) +0.6963*maxP200+(−0.0401*age*maxP200), wherein age means the test subject's age in years, sex means, in the case of a male test subject, the value of 0, and in the case of a female test subject the value of 1, lnDeltaF4 means the natural log of the absolute value, in microvolts of the Delta wave band, as taken at the electrode placement location F4, lnDeltaCZ means the natural log of the absolute value, in microvolts of the Delta wave band, as taken at the electrode placement location CZ, and MaxP200 means the maximum positive voltage potential at either the F3 or F4 electrodes, in microvolts, of the visually evoked response at a time of approximately 200 milliseconds after termination of the visual of said paradigms.

7. A method of determining the probability of ruminating behavior in a person of known age, sex and known to be using medication at the time of testing, using an electroencephalographic machine operable for reading human brain waves, a computer operable for receiving the output of said electroencephalographic machine, a device operable to display a paradigm of a pre-selected design, illumination, and frequency, said computer also capable of synchronizing the recording and averaging said brains waves when the paradigm is illuminated, which comprises:

attaching the electrodes of an electroencephalographic machine to the scalp of a person in accordance with the American Electroencephalographic Society's Electrode Placement International 10-20 Standard System for measuring a person's brain waves;

positioning said person to view a paradigm to visually evoke a potential in said person's brain;

displaying to said person a plurality of sequentially displayed paradigms and simultaneously measuring the brain waves of said person for each of said displayed paradigms during the time of display;

averaging said brain waves to determine the visually evoked response to said displays of said paradigms;

measuring the maximum amplitude, in microvolts, of said visually evoked response over a period of time of approximately 500 ms after termination of each of said displays of said paradigms;

transmitting to said person a plurality of audio signals and simultaneously measuring the brain waves of said person for each of the audio signals during the time said auditory signals are being transmitted;

averaging said brain waves to determine the auditory evoked response to said transmissions of said audio signals;

measuring the maximum amplitude, in microvolts, of said auditory evoked response at a plurality of points in time over approximately 500 ms of time after termination of each of the transmissions of said audio signals;

measuring the absolute power of the Delta frequency band waves at electrodes F3, F4 and O1; and computing the probability of ruminating behavior using the algorithm ln(P[ruminating])=+1.7726+(−0.1044*age)+0.6774*sex+2.0495*lnDeltaF3)+(−1.993*lnDeltaO1)+(−0.1199*maxP100)+0.157*maxP200, wherein P[ruminating] means the probability of ruminating behavior, age means the person's age in years, sex has a value of 0 if said person is a male and a value of 1 if said person is a female, lnDeltaF3 means the log of the absolute power of the Delta frequency band taken at electrode F3, lnDeltaF4 means the log of the absolute power of the Delta frequency band taken at electrode F4, lnDeltaO1 means the log of the absolute power of the Delta frequency band taken at electrode O1, MaxP100 means the maximum positive voltage potential at either the O1 or the O2 electrodes, in microvolts, of the visually evoked response at a time of approximately 100 milliseconds after termination of the visual of said paradigms, and MaxP200 means the maximum positive voltage potential at either the F3 or F4 electrodes, in microvolts, of the visually evoked response at a time of approximately 200 milliseconds after termination of the visual of said paradigms.

8. An apparatus for determining the probability of ruminating behavior in a person of know age, sex and known to be using medication, which comprises:

an electroencephalographic machine having a plurality of electrodes for attachment to the scalp of a person in accordance with the American Electroencephalographic Society's Electrode Placement International 10-20 Standard System for measuring a person's brain waves;

means for displaying to said person a plurality of sequentially displayed paradigms and simultaneously measuring the brain waves of said person for each of said displayed paradigms during the time of display;

means for averaging said brain waves to determine the visually evoked response to said displays of said paradigms;

means for assessing the maximum amplitude, in microvolts, of said visually evoked response over a period of time of approximately 500 ms after termination of each of said displays of said paradigms;

means for transmitting to said person a plurality of audio signals and simultaneously measuring the brain waves of said person for each of the audio signals during the time said auditory signals are being transmitted;

means for averaging said brain waves to determine the auditory evoked response to said transmissions of said audio signals;

means for measuring the maximum amplitude, in microvolts, of said auditory evoked response at a plurality of points in time over approximately 500 ms of time after termination of each of the transmissions of said audio signals;

means for measuring the absolute power of the Delta frequency band at electrodes F3, F4 and O1;

means for computing the probability of ruminating behavior using the algorithm ln(P[ruminating])=+1.7726+(−0.1044*age)+0.6774*sex+2.0495*lnDeltaF3)+(−1.993*lnDeltaO1) +(−0.1199*maxP100)+ 0.157*maxP200, wherein P[ruminating] means the probability of ruminating behavior, age means the person's age in years, sex has a value of 0 if said person is a male and a value of 1 if said person is a female, lnDeltaF3 means the log of the absolute power of the Delta frequency band taken at electrode F3, lnDeltaF4 means the log of the absolute power of the Delta frequency band taken at electrode F4, lnDeltaO1 means the log of the absolute power of the Delta frequency band taken at electrode O1, MaxP100 means the maximum positive voltage potential at either the O1 or the O2 electrodes, in microvolts, of the visually evoked response at a time of approximately 100 milliseconds after termination of the visual of said paradigms, and MaxP200 means the maximum positive voltage potential at either the F3 or F4 electrodes, in microvolts, of the visually evoked response at a time of approximately 200 milliseconds after termination of the visual of said paradigms.

* * * * *